United States Patent [19]

Alferness

[11] 4,355,642
[45] Oct. 26, 1982

[54] MULTIPOLAR ELECTRODE FOR BODY TISSUE

[75] Inventor: Clifton A. Alferness, Woodinville, Wash.

[73] Assignee: Physio-Control Corporation, Redmond, Wash.

[21] Appl. No.: 206,638

[22] Filed: Nov. 14, 1980

[51] Int. Cl.³ .............................................. A61B 5/04
[52] U.S. Cl. .................... 128/642; 128/785; 128/419 P
[58] Field of Search ................ 128/642, 698, 784–786, 128/419 P

[56] References Cited

U.S. PATENT DOCUMENTS

| Re. 28,990 | 10/1976 | Hon et al. | 128/785 |
|---|---|---|---|
| 3,216,424 | 11/1965 | Chardack | 128/785 |
| 3,253,595 | 5/1966 | Murphy, Jr. et al. | 128/785 |
| 3,313,293 | 4/1967 | Chesebrough et al. | 128/785 |
| 3,416,534 | 12/1968 | Quinn | 128/785 |
| 3,472,234 | 10/1969 | Tachick | 128/785 |
| 3,737,579 | 6/1973 | Bolduc | 128/785 |
| 3,750,650 | 8/1973 | Ruttgers | 128/785 |
| 3,827,428 | 8/1974 | Hon et al. | 128/785 |
| 3,974,834 | 8/1976 | Kane | 128/785 |
| 4,000,745 | 1/1977 | Goldberg | 128/785 |
| 4,010,758 | 3/1977 | Rockland et al. | 128/785 |
| 4,026,301 | 5/1977 | Friedman et al. | 128/785 |
| 4,157,710 | 6/1979 | Abitbol | 128/785 |
| 4,180,080 | 12/1979 | Murphy | 128/785 |

FOREIGN PATENT DOCUMENTS 133401  1/1979  Fed. Rep. of Germany ...... 128/785

*Primary Examiner*—Lee S. Cohen
*Attorney, Agent, or Firm*—Christensen, O'Connor, Johnson & Kindness

[57] ABSTRACT

A bipolar electrode 10 capable of sensing the electrical activity in a localized portion of body tissue includes a disc 12 having a surface 12A adapted to be brought into proximity to a surface of the body tissue, and an inner electrode or conductive spike 14 and a first outer electrode or helix 16 that are supported by disc 12 and that extend from surface 12A. Corkscrew 16 surrounds spike 14, and the tip 16A of helix 16 is located at a greater distance away from surface 12A than is tip 14A of spike 14. Tripolar electrodes 30, 50 utilize this structure along with a second outer electrode or helix 38 (in tripolar electrode 30) and an annular conductive ring 58 (in tripolar electrode 50) for respectively applying pacing and defibrillation pulses to the heart.

18 Claims, 5 Drawing Figures

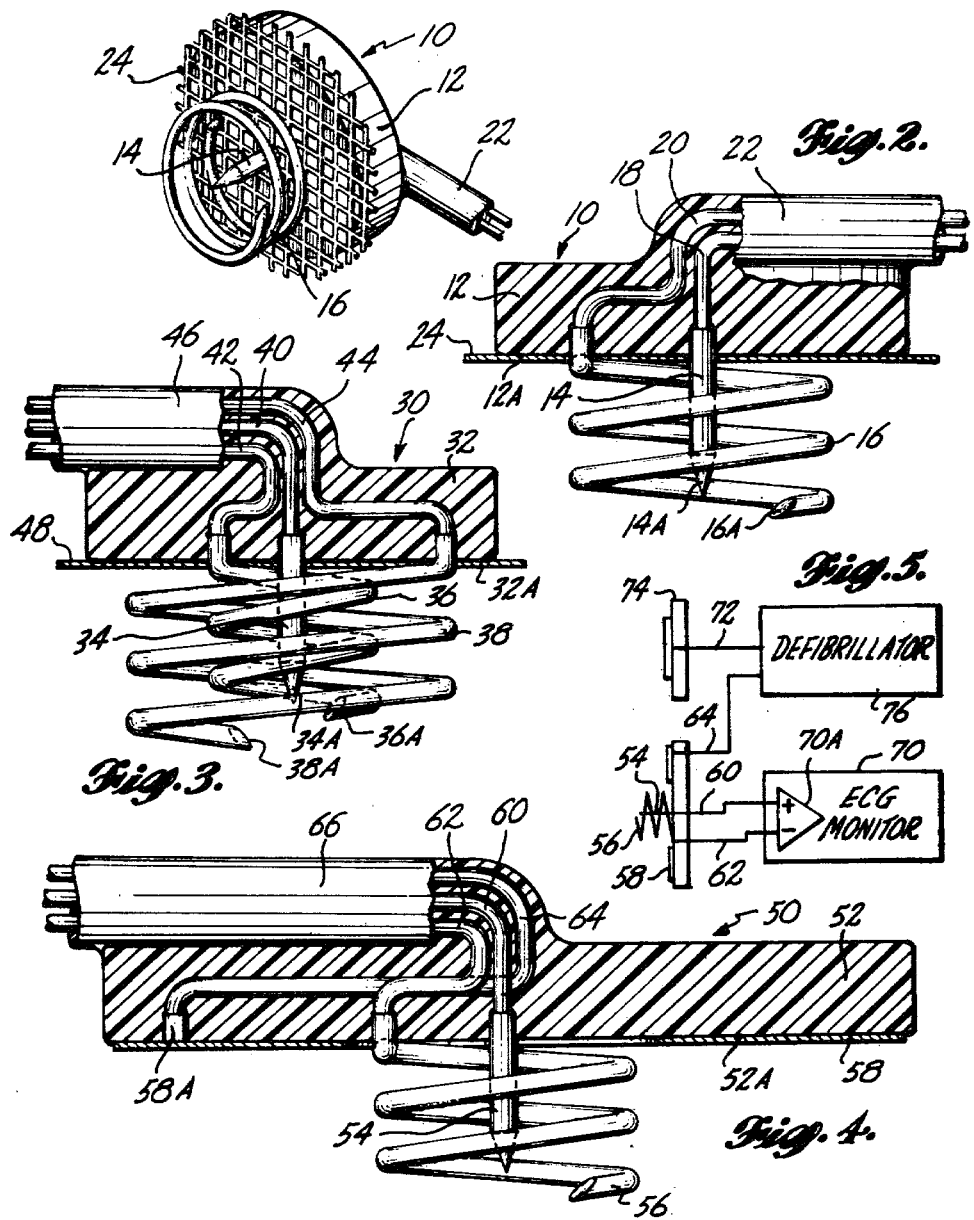

MULTIPOLAR ELECTRODE FOR BODY TISSUE

FIELD OF THE INVENTION

This invention generally relates to electrodes that are designed to be implanted in body tissue such as the cardiac or heart muscle, and more particularly, to a multipolar form of such an electrode which is capable of sensing the electrical activity in a localized portion of the body tissue.

BACKGROUND OF THE INVENTION

In a muscle such as the heart, contraction of each muscle cell is preceded by depolarization thereof in which the electric potential at the inside of the cell becomes positive with respect to the electric potential at the outside of the cell. Depolarization usually starts in one portion of the muscle, and then passes throughout the remainder of the muscle. As a result, a wave of depolarization, or negative potential change at the outside of the cells, passes throughout the muscle. The well-known techniques for monitoring the electrical activity of the heart involve the use of two or more unipolar (i.e., single) electrodes that are placed at separate locations on the body. Such electrodes may be external electrodes, each of which typically comprises a flat conductive disc which is affixed to the skin of the body, or internal electrodes, each of which typically comprises a conductive helix that is implanted into the heart. In use, the signals from a pair of such electrodes are coupled to corresponding inputs of a differential preamplifier on whose output accordingly appears an ECG signal having the well-known PQRST waveform. It is known that the characteristics of this waveform differ, depending on the relative placement of the pair of electrodes that are used to detect the ECG signal. Accordingly, by selective placement of the pair of electrodes and by appropriate filtering of the ECG signal, information may be obtained as to the electrical activity in any one of a plurality of sections through the heart. However, the information that is so obtained cannot be localized to any specific incremental portion of the heart, and there is accordingly no way to detect the amplitude and time occurrence of depolarization (or other electrical activity) in any such incremental portion.

Use of such unipolar electrodes also causes certain problems when the heart is being defibrillated by the application of a defibrillation pulse thereto or is being regulated by the application of a repetitive pacing pulse thereto. The amplitudes of such defibrillation and pacing pulses are much greater than the amplitude of the wave of depolarization that is passing through the heart. As a result, the differential preamplifier that is used to detect the ECG signal must be protected against these pulses by appropriate protection circuitry which prevents the high energy of the defibrillation or pacing pulses from reaching the differential preamplifier. Unfortunately, such protection circuitry limits the response to the differential preamplifier so that a predetermined period of time must occur after the occurrence of a defibrillation or pacing pulse until the electrical activity of the heart can again be monitored.

Further, the ECG signal detected by unipolar electrodes is oftentimes obscured by noise comprising interference from sources thereof external to the body, such as electromagnetic (EMI) interference, radiofrequency (RFI) interference, or power line (e.g., 60 Hz) interference, or comprising artifact from sources thereof internal to the body, such as myopotentials (muscle potentials) in other muscles in the body.

The use of unipolar electrodes is also disadvantageous in that a multiplicity of electrical and mechanical connections must be made to the body. Although bipolar (i.e., double) electrodes have been proposed which include a pair of electrodes associated with the same physical structure and which accordingly require only a single mechanical connection to the body, these bipolar electrodes have not been capable of accurately sensing the electrical activity in any localized or incremental portion of a muscle such as the heart.

It is therefore an object of this invention to provide an improved multipolar electrode for body tissue.

It is a further object of this invention to provide such an electrode which is capable of sensing the electrical activity in a localized portion of the body tissue.

It is yet a further object of this invention to provide such an electrode which can be used both for the application of electrical signals to the body tissue and for the sensing the electrical activity in a localized portion of the body tissue.

It is another object of this invention to provide such an electrode which, when used to apply an electrical pulse to the body tissue, can also be used, without significant loss of response time, to sense substantially contemporaneous electrical activity in a localized portion of the body tissue.

It is yet another object of this invention to provide such an electrode which is capable of sensing the electrical activity in a localized portion of the body tissue in the presence of interference or artifact which would obscure the ECG signal detected by conventional unipolar electrodes.

It is still another object of this invention to provide such an electrode which is simple to fabricate from readily-available, inexpensive materials, and which is relatively easy to install and use.

SUMMARY OF THE INVENTION

Briefly, these objects, and other objects and advantages that will be apparent to those of ordinary skill in the art from a consideration of the following portion of the specification, are achieved in a multipolar electrode that is adapted to be implanted in body tissue. The electrode comprises a base member, an inner electrode and a first outer electrode, with at least a portion of each of the inner and first outer electrodes being composed of conductive material. The base member has a base member surface adapted to be brought into proximity to a surface of the body tissue, and the inner and first outer electrodes are supported by the base member and extend in a predetermined direction from the base member surface thereof. The first outer electrode is in the form of a helix which surrounds the inner electrode, with the conductive portion of the first outer electrode extending further from the base member surface than the conductive portion of the inner electrode.

In a preferred embodiment, the inner electrode includes a substantially linear conductive wire that terminates in a sharpened tip, and the base member includes a substantially cylindrical disc having a substantially planar, base member surface. The inner electrode, or "spike" is centrally located in the disc, and the first outer electrode is concentric with this spike.

In another form of the multipolar electrode, a second outer electrode of conductive material is provided which is supported by the base member and which extends from the base member surface thereof. The second outer electrode may include either an annular conductive ring which is located on the base member surface, or, a second helix which surrounds the helix of the first outer electrode.

The inner electrode and the first outer electrode are used to detect electrical activity in a localized area of the body tissue, such as the heart, and the annular ring and the second helix may be used to apply defibrillation and pacing pulses to the heart, respectively.

BRIEF DESCRIPTION OF THE DRAWINGS

The invention can best be understood by reference to the following portion of the specification, taken in conjunction with the accompanying drawings in which:

FIG. 1 is a pictorial view of a bipolar electrode constructed according to the teachings of the present invention;

FIG. 2 is a cross-sectional, elevational view of the bipolar electrode of FIG. 1;

FIG. 3 is a cross-sectional, elevated view of a tripolar electrode constructed according to the teachings of the present invention and particularly adapted for the application of a pacing pulse to the heart;

FIG. 4 is a cross-sectional, elevational view of a tripolar electrode constructed according to the teachings of the present invention and particularly adapted for the application of a defibrillation pulse to the heart; and, FIG. 5 is a block diagram illustrating the electrical connections to the tripolar electrode of FIG. 4.

DESCRIPTION OF THE PREFERRED EMBODIMENT

Referring now to FIGS. 1 and 2, the bipolar electrode 10 illustrated therein is particularly adapted for sensing the electrical activity in a localized portion of the heart and includes a base member or disc 12, of electrically-insulating material, in which is supported and from which extends an inner electrode consisting of a conductive spike 14. As best seen in FIG. 2, disc 12 has a substantially planar surface 12A, and spike 14 is centrally located in disc 12 so as to extend at right angles from surface 12A and to terminate in a tip 14A at a certain distance from surface 12A. An outer electrode consisting of a conductive helix 16 is also supported in and extends from disc 12, with helix 16 being concentric with spike 14 and terminating in a tip 16A. It is important to note that the distance between tip 16A of helix 16 and surface 12A is greater than the distance between tip 14A of spike 14 and surface 12A. Insulated electrical leads 18, 20 are soldered or otherwise electrically connected to spike 14 and helix 16, and are arranged in a cable 22 so as to permit connection of leads 18, 20 (by means not illustrated) to the respective inputs of the differential preamplifier within a conventional ECG monitor. The bipolar electrode is completed by a mesh 24 of Dacron ™ synthetic fibers that is affixed to disc 12 in proximity to surface 12A.

To implant bipolar electrode 10 into the heart, a suitable surgical incision is made in the chest and in the pericardial sac surrounding the heart. Bipolar electrode 10 is then grasped by a tool (not illustrated) and inserted through the incision until the tip 16A of helix 16 comes into contact with the heart. As the tool is thereafter rotated, both helix 16 and spike 14 enter into the heart until mesh 24 contacts the heart surface and surface 12A is proximate to the heart surface, whereupon the tool is removed and the surgical incision is closed. As with conventional unipolar electrodes, mesh 24 permits bipolar electrode 10 to be maintained in place on the heart as the surrounding body tissue grows into mesh 24 following implantation.

When so implanted, bipolar electrode 10 senses the electrical activity only in the specific portion of the heart between helix 16 and spike 14. Because helix 16 surrounds spike 14, and extends into the heart further than spike 14, any wave of depolarization always reaches helix 16 before spike 14, notwithstanding the direction from which the wave of depolarization is coming. As a result, the potential difference between spike 14 and helix 16 represents only the depolarization that is occurring in the portion of the heart between helix 16 and spike 14, and the potential on spike 14 is always positive with respect to that on helix 16 upon depolarization.

Spike 14 and helix 16 may each be fabricated from platinum iridium wire, and disc 12 may be fabricated from a medical grade of silicone rubber. To fabricate the electrode, spike 14 and helix 16 are supported by a jig in the desired spatial relationship, electrical leads 18, 20 are brought out from cable 22 and electrically connected to spike 14 and helix 16, and disc 12 is molded in place by a conventional molding process. Although the relative dimensions of spike 14, helix 16 and disc 12 may be varied to fit a specific application, the following dimensions may be used as an example:

| | |
|---|---|
| diameter of disc 12 | = 9 mm; |
| diameter of wire used to form spike 14 and helix 16 | = 0.3 mm; |
| distance between point 14A and surface 12A | = 2 mm; |
| distance between tip 16A and surface = | 3.5 mm; |
| diameter of helix 16 | = 3 mm. |

A tripolar electrode 30 useful in applying a pacing pulse to the heart and sensing the electrical activity in a localized portion of the heart is illustrated in FIG. 3. Supported in and extending from a disc 32, of electrically-insulating material, are an inner electrode consisting of a conductive spike 34, a first outer electrode consisting of a conductive helix 36, and a second outer electrode consisting of a conductive helix 38. Both helix 36 and helix 38 are concentric with spike 34, and helix 38 has a greater diameter than that of helix 36. Spike 34 and helix 36 terminate in respective tips 34A and 36A located at progressively further distances from a lower, substantially planar surface 32A of disc 32, and helix 38 terminates in a tip 38A which may be located at any desired distance from surface 32A. Insulated electrical leads 40, 42 and 44 are soldered or otherwise electrically connected to spike 34, helix 36 and helix 38, respectively, and are arranged in a cable 46 extending from disc 32. Tripolar electrode 30 is completed by a mesh 48, again of Dacron ™ synthetic fibers, that is affixed to disc 32 in proximity to surface 32A.

In use, leads 40 and 42 are connected to corresponding inputs of the differential preamplifier within an ECG monitor, as with the corresponding leads 18, 20 of the bipolar electrode 10 in FIGS. 1 and 2. Lead 46 and another lead (not illustrated) are connected to the outputs of a conventional pacemaker, with the other lead going to an indifferent electrode (also not illustrated) which may be a conventional unipolar electrode implanted at a separate location on the heart or which may comprise the second outer electrode of another tripolar electrode of the type shown in FIG. 3. The pacing pulses from the pacemaker are accordingly applied to the entire heart, but only that electrical activity within the portion of the heart between helix 36 and spike 34 is detected by bipolar electrode 30.

The materials and method of construction of tripolar electrode 30 may be identical to those previously described for bipolar electrode 10. Although the relative dimensions of spike 34, helix 36 and helix 38 may be varied to fit a specific application, the following dimensions may be used as an example:

| | |
|---|---|
| diameter of disc 32 | = 9 mm; |
| diameter of wire used to form spike 34, helix 36 and helix 38 | = 0.3 mm; |
| distance between tip 34A and surface 32A | = 2 mm; |
| distance between tip 36A and surface 32A | = 3.5 mm; |
| diameter of helix 36 | = 3 mm; |
| distance between tip 38A and surface 32A | = 3.5 mm; |
| diameter of helix 38 | = 7 mm. |

A tripolar electrode 50 useful in applying a defibrillation pulse to the heart and sensing the electrical activity in a localized portion of the heart is illustrated in FIG. 4. As with tripolar electrode 30 and bipolar electrode 10, tripolar electrode 50 includes a disc 52 having a lower, substantially planar surface 52A, an inner electrode consisting of a spike 54, and a first outer electrode consisting of a helix 56. A second outer electrode consisting of an annular, conductive ring 58 is supported from disc 52 and is located on surface 52A thereof, with ring 58 being concentric with spike 54 and helix 56. Electrical leads 60, 62 and 64 are soldered or otherwise electrically connected to spike 54, helix 56, and to a projection 58A on disc 58, respectively, and are arranged in a cable 66 extending from disc 52.

In use (reference FIG. 5), leads 60 and 62 are connected to corresponding inputs of a differential preamplifier 70A within a conventional ECG monitor 70. Lead 64 and a lead 72 from a conventional plate electrode 74 (which may also comprise the ring of another tripolar electrode similar to that illustrated in FIG. 4) are connected to the output of a conventional defibrillator 76. A defibrillation pulse from defibrillator 76 appearing on leads 64, 72 is accordingly applied to the entirety of the heart, but only the electrical activity within that portion of the heart between spike 54 and helix 56 is detected by ECG monitor 70. From a consideration of FIG. 5, it will be appreciated that the defibrillation pulse appears as a substantially common mode signal on leads 60 and 62 going to differential preamplifier 70A, so that the resultant potential difference across the inputs of differential preamplifier 70A is substantially zero. Accordingly, differential preamplifier 70A is not overloaded by the defibrillation pulse, and sensing of the electrical activity of the heart can commence immediately following termination of the defibrillation pulse. A similar statement can be made for the operation of the tripolar electrode 30 in FIG. 3, e.g., each pacing pulse appears as a substantially common mode signal on leads 40 and 42 respectively connected to spike 34 and helix 36.

The materials and method of construction of tripolar electrode 50 may be identical to those previously described for tripolar electrode 30 and bipolar electrode 10. Although the relative dimensions of spike 54 and helix 56 may be varied to suit a particular application, the diameter of ring 58, and the total surface area thereof, should be chosen so as to deliver the relatively high-energy defibrillation pulse over a relatively large area of the heart. As an example, ring 58 may have an inner diameter of 4 mm, an outer diameter of 9 mm, and disc 52 may have a correspondingly larger diameter.

By using a bipolar electrode structure in which the outer electrode surrounds the inner or central electrode and extends further into the heart (or other body tissue) further than the inner electrode, certain advantages in addition to those previously discussed are obtained. For example, the P wave in the normal ECG signal, which represents depolarization in the upper portion of the heart, may be substantially eliminated by placing the bipolar electrode in other portions of the heart. The R wave in the normal ECG signal represents the wave of depolarization passing through the ventricles of the heart and the T wave in the normal ECG signal represents a wave of repolarization passing through the ventricles of the heart. Depending on the placement of conventional unipolar electrodes, the polarities of the R waves may differ, as may the polarities of the T waves. With the use of the bipolar electrode, depolarization always has a predetermined polarity, and repolarization usually has an opposite polarity. Also, the shielding effect afforded by the outer electrode in the bipolar electrode makes the signal developed therefrom relatively free of potential changes occurring elsewhere in the heart and of potential changes resulting from the application of defibrillation and pacing pulses to the heart, as previously discussed, but also relatively free of noise comprising interference and artifact.

While the invention has been described with reference to a preferred embodiment, it is to be clearly understood that the invention is not limited thereto. It is not essential that the inner and outer electrodes be entirely composed of conductive material. For example, it may be desirable in a specific application to have the tip of the inner electrode extend further from the bodytissue proximate surface of the base member (e.g., surface 12A in FIG. 2) than the tip of the first outer electrode. In such an application, the portion of the inner electrode adjacent the tip thereof may be composed of electrically-insulating material. Likewise, it also may be desirable that the portion of the first outer electrode adjacent the tip thereof be also composed of electrically-insulating material. It will be appreciated that the objects and advantages of the bipolar electrode structure previously described will be achieved in such situations, provided that the conductive portion of the first outer electrode extends further from the body-tissue proximate surface of the base member than does the conductive portion of the inner electrode. Therefore, the scope of the invention is to be interpreted only in conjunction with the appended claims.

The embodiments of the invention in which an exclusive property or privilege is claimed are defined as follows:

1. A multipolar electrode that is adapted to be implanted in body tissue, said electrode comprising:
   a base member having a surface adapted to be brought into proximity to a surface of the body tissue;

an inner electrode supported by said base member and extending in a predetermined direction from said base member surface, at least a portion of said inner electrode being composed of conductive material;

a first outer electrode supported by said base member and extending in said predetermined direction from said base member surface, at least a portion of said first outer electrode being composed of conductive material, said first outer electrode being in the form of a helix which surrounds said inner electrode and said conductive portion of said first outer electrode extending further in said predetermined direction from said base member surface than said conductive portion of said inner electrode;

a first electrical lead connected to said conductive portion of said inner electrode; and, a second electrical lead connected to said conductive portion of said first outer electrode.

2. A multipolar electrode as recited in claim 1, wherein said inner electrode includes a substantially linear conductive wire that terminates in a sharpened tip at a first predetermined distance from said base member surface, and wherein said first outer electrode includes a conductive wire that terminates in a sharpened tip at a second predetermined distance from said base member surface, said second predetermined distance being greater than said first predetermined distance.

3. A multipolar electrode as recited in claim 2, wherein said first outer electrode is concentric with said inner electrode.

4. A multipolar electrode as recited in claim 1, wherein said base member includes a substantially cylindrical disc, and wherein said base member surface comprises a substantially planar surface of said disc.

5. A multipolar electrode as recited in claim 4, wherein said inner electrode is centrally located on said substantially planar surface.

6. A multipolar electrode as recited in claims 4 or 5, wherein said inner electrode includes a substantially linear conductive wire that terminates in a sharpened tip at a first predetermined distance from said substantially planar surface, and wherein said first outer electrode includes a conductive wire that terminates in a sharpened tip at a second predetermined distance from said substantially planar surface, said second predetermined distance being greater than said first predetermined distance.

7. A mutlipolar electrode as recited in claim 6, wherein said first outer electrode is concentric with said inner electrode.

8. A multipolar electrode as recited in claim 6, wherein said inner electrode and said first outer electrode each extend at substantially right angles from said substantially planar surface.

9. A multipolar electrode as recited in claim 1, wherein said base member is composed of an electrically-insulating material.

10. A multipolar electrode as recited in claim 1, further comprising a second outer electrode which is supported by said base member and which extends in said predetermined direction from said base member surface, at least a portion of said second outer electrode being composed of conductive material; and a third electrical lead connected to said conductive portion of said second outer electrode.

11. A multipolar electrode as recited in claim 10, wherein said second outer electrode includes an annular conductive ring which is located on said base member surface and which has a diameter that is greater than the diameter of said first outer electrode.

12. A multipolar electrode as recited in claim 11, wherein said inner electrode includes a substantially linear conductive wire that terminates in a sharpened tip at a first predetermined distance from said base member surface, and wherein said first outer electrode includes a conductive wire that terminates in a sharpened tip at a second predetermined distance from said base member surface, said second predetermined distance being greater than said first predetermined distance.

13. A multipolar electrode as recited in claim 12, wherein said first and said second outer electrodes are each concentric with said inner electrode.

14. A multipolar electrode as recited in claim 10, wherein said second outer electrode includes a conductive wire which is in the form of a helix and which surrounds said inner electrode.

15. A multipolar electrode as recited in claim 14, wherein said second outer electrode has a diameter that is greater than the diameter of said first outer electrode and wherein said second outer electrode surrounds said first outer electrode.

16. A multipolar electrode as recited in claim 15, wherein said inner electrode includes a substantially linear conductive wire that terminates in a sharpened tip at a first predetermined distance from said base member surface, and wherein said first outer electrode includes a conductive wire that terminates in a sharpened tip at a second predetermined distance from said base member surface, said second predetermined distance being greater than said first predetermined distance.

17. A multipolar electrode as recited in claim 15, wherein said first and said second outer electrodes are each concentric with said inner electrode.

18. A multipolar electrode as recited in claims 1 or 10, further comprising a mesh of synthetic fibers which is supported from said base member in proximity to said base member surface.

* * * * *

UNITED STATES PATENT AND TRADEMARK OFFICE
CERTIFICATE OF CORRECTION

PATENT NO. : 4,355,642

DATED : October 26, 1982

INVENTOR(S) : Clifton A. Alferness

It is certified that error appears in the above-identified patent and that said Letters Patent are hereby corrected as shown below:

Column 4, line 38 (Line 7 of table): "surface =   3.5mm;" is changed to --surface 12A   = 3.5mm;--

Column 6, lines 44 and 45: "bodytissue" is changed to --body-tissue--

Signed and Sealed this

Twenty-second Day of March 1983

[SEAL]

Attest:

GERALD J. MOSSINGHOFF

Attesting Officer

Commissioner of Patents and Trademarks